United States Patent
Sielcken et al.

(10) Patent No.: US 7,102,033 B2
(45) Date of Patent: Sep. 5, 2006

(54) CONTINUOUS HYDROFORMYLATION PROCESS FOR PRODUCING AN ALDEHYDE

(75) Inventors: Otto Erik Sielcken, Sittard (NL); Hubertus Adrianus Smits, Maastricht (NL); Imre Toth, Geleen (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/474,680

(22) PCT Filed: Apr. 11, 2002

(86) PCT No.: PCT/NL02/00238

§ 371 (c)(1),
(2), (4) Date: May 3, 2005

(87) PCT Pub. No.: WO02/083604

PCT Pub. Date: Oct. 24, 2002

(65) Prior Publication Data

US 2006/0052644 A1    Mar. 9, 2006

(30) Foreign Application Priority Data

Apr. 13, 2001 (EP) .................................. 01201369

(51) Int. Cl.
*C07C 45/50* (2006.01)
(52) U.S. Cl. ...................................... 568/451; 568/454
(58) Field of Classification Search .................... None
See application file for complete search history.

(56) References Cited

U.S. PATENT DOCUMENTS

| | | | |
|---|---|---|---|
| 4,148,830 A | 4/1979 | Pruett | 260/604 |
| 4,518,809 A | 5/1985 | Forster | 568/840 |
| 4,528,403 A | 7/1985 | Tano | 568/454 |
| 4,528,404 A | 7/1985 | Oswald | 568/454 |
| 4,668,651 A | 5/1987 | Billig | 502/159 |
| 4,717,775 A | 1/1988 | Billig | 568/454 |
| 4,769,498 A | 9/1988 | Billig | 568/454 |
| 5,288,918 A | 2/1994 | Maher | 568/454 |
| 5,710,306 A | 1/1998 | Snijder | 558/93 |
| 5,763,670 A | 6/1998 | Billig | 568/454 |
| 6,090,987 A | 7/2000 | Billig | 568/454 |

OTHER PUBLICATIONS

International Search Report from international application PCT/NL02/00238.

*Primary Examiner*—Sikarl A. Witherspoon
(74) *Attorney, Agent, or Firm*—Mayer, Brown, Rowe & Maw LLP

(57) ABSTRACT

A continuous hydroformylation process for producing an aldehyde comprising 1) reacting an olefinically unsaturated compound, carbon monoxide and hydrogen in the presence of a rhodium-organobisphosphite complex catalyst at a partial pressure of carbon monoxide and hydrogen, and 2) exposing a mixture comprising at least a portion of the catalyst of 1) to a gaseous mixture comprising hydrogen at a pressure that is greater than the partial pressure of carbon monoxide and hydrogen during the reaction.

10 Claims, No Drawings

CONTINUOUS HYDROFORMYLATION PROCESS FOR PRODUCING AN ALDEHYDE

CROSS REFERENCE TO RELATED APPLICATION

This application is the National Phase of International Application PCT/NL02/00238 filed Apr. 11, 2002 which designated the U.S., and that International Application was published under PCT Article 21(2) in English.

The invention relates to a continuous hydroformylation process for producing an aldehyde comprising 1) reacting an olefinically unsaturated compound, carbon monoxide and hydrogen in the presence of a rhodium-organobisphosphite complex catalyst at a partial pressure of carbon monoxide and hydrogen.

It is well known in the art that aldehydes may be readily produced by reacting an olefinically unsaturated compound with carbon monoxide and hydrogen in the presence of a rhodium-organophosphorous ligand complex catalyst and that preferred process involved continuous hydroformylation and recycling of the catalyst solution such as disclosed, for example, in U.S. Pat. Nos. 4,148,830; 4,717,775; and 4,769,498. Organophosphites, especially organobisphosphites, have proven to be among the ligands of choice in rhodium catalyzed hydroformylation reactions because such complexes exhibit exceptional activity and regioselectivity in this reaction. For instance, U.S. Pat. Nos. 4,668,651 and 4,769,498 fully detail such hydroformylation.

However, although rhodium catalyzed hydroformylation reactions have enjoyed a wealth of commercial development, efficiency and cost associated with these processes remain a primary concern, especially in light of the scarcity and high price of rhodium metal, as well as the costs associated with organobisphosphite ligands. Traditional attempts to improve the reaction rate, as well as reduce costly decomposition pathways of the metal complex catalysts and/or ligand have focused on ligand choice, as described above, or reaction conditions. For example, U.S. Pat. Nos. 5,288,918 and 5,763,670 describe catalyst protection and increased longevity through the addition of additives, or manipulation of the reaction conditions.

Yet the rate of the hydroformylation reaction is often reduced by the presence of other compounds in the reaction mixture which may form more stable, yet less reactive rhodium species. Such compounds produce rhodium complexes which do not catalyze the desired hydroformylation reaction and therefore slow down the rate of hydroformylation, require greater amounts of rhodium, and turn, increase the cost of the hydroformylation process.

One such class of compounds are organic species which contain multiple alkene functionalities, usually alkadienes. These compounds act as a type of poison towards the metal center by complexing or reacting with it. The resulting rhodium alkadiene complex is thus prevented from entering the desired reaction pathway of hydroformylation, because such a pathway would require the energetically favored coordinated alkadiene to be first displaced in order to react with the desired olefinically unsaturated compound, carbon monoxide, and hydrogen.

Since many of the olefinically unsaturated compounds which are commercially hydroformylated are synthesized from, or contain as impurities, alkadienes, these catalyst poisons are often present in typical hydroformylation processes. As a result, much rhodium metal is prevented from participating in the hydroformylation process, which corresponds to increased production costs for aldehydes produced by these processes. Accordingly, a method by which these poisons could be prevented from interfering with the catalyst would be a great improvement in the hydroformylation process.

The object of the invention is to prevent or at least minimize decrease in reaction rate in rhodium-organobisphosphite complex catalyzed continuous hydroformylation processes.

This object is achieved in that the process also comprises 2) exposing a mixture comprising at least a portion of the catalyst of 1) to a gaseous mixture comprising hydrogen at a pressure that is greater than the partial pressure of carbon monoxide and hydrogen during the reaction.

The pressure at which the mixture comprising at least a portion of the catalyst of 1) is treated, i.e. the pressure used in step 2) is also referred to as activating pressure. By activating pressure, it is meant a pressure which is greater than the partial sum of the pressures of carbon monoxide and hydrogen during the hydroformylation reaction.

The gaseous mixture comprises hydrogen or preferably comprises hydrogen and carbon monoxide.

It has been found that alkadiene and especially conjugated alkadiene poisoning of the catalyst is minimized or reversed by carrying out a part of said process at an activating pressure of hydrogen or at activating pressures of hydrogen and carbon monoxide.

Accordingly, the subject invention encompasses reversing or minimizing the catalyst deactivation associated with alkadiene poisoning of rhodium-organobisphosphite complex catalyzed hydroformylation processes for producing aldehydes, by treating a mixture comprising at least a portion of the catalyst used in the hydrofomylation reaction at an activating pressure of hydrogen or of carbon monoxide and hydrogen. Preferably, the activating pressure is a pressure between 3 MPa and 20 MPa of a mixture of gases comprising hydrogen or comprising hydrogen and carbon monoxide. Still more preferably the activating pressure is between between 3 and 10 MPa. If it is chosen to reverse or minimize the catalyst deactivation associated with alkadiene poisoning of rhodium-organobisphosphite complex catalyzed hydroformylation processes for producing aldehydes, by performing part of this process at an activating pressure of carbon monoxide and hydrogen, the pressure is preferably equal to the combined hydrogen and carbon monoxide pressure. The molar ratio of hydrogen and carbon monoxide is between 10:1 and 1:10, preferably between 6:1 and 1:1 and more preferably between 2:1 and 1:1. The temperature at which the the catalyst deactivation associated with alkadiene poisoning of rhodium-organobisphosphite complex catalysts is reversed, prevented or at least minimized is preferably between 25° C. and 200° C., more preferably from 70° C. to 120° C. and most preferably from 90° C. to 100° C.

The mixture which in the process of the invention is exposed to a gaseous mixture comprising hydrogen at an activating pressure greater than the partial pressure of hydrogen and carbon monoxide during the hydroformylation reaction is preferably at least a portion of the hydroformylation reaction mixture or at least a portion of the reaction mixture obtained between the hydroformylation reaction zone and the separation zone in which separation zone the desired aldehyde product is separated off.

A preferred embodiment of the present invention is a continuous hydroformylation process for producing an aldehyde comprising reacting a rhodium-organobisphosphite complex catalyst, carbon monoxide, hydrogen, and an olefinically unsaturated compound, to form a hydroformylation reaction mixture wherein said hydroformylation reaction mixture is distilled into an aldehyde product containing stream and a recyclable catalyst containing stream, and wherein said carbon monoxide and hydrogen are both maintained at independent minimum partial pressures during the reaction, and wherein a least a portion of said hydroformylation reaction mixture is exposed to an activating pressure of a gaseous mixture comprising hydrogen or comprising hydrogen and carbon monoxide prior to distillation which activating pressure is greater than said minimum pressures. Generally, the reaction mixture removed from the hydroformylation reaction zone (the hydroformylation reaction mixture) is subjected to a pressure reduction so as to volatilize and remove a substantial portion of the unreacted gases dissolved in the reaction mixture and then pass the so-obtained liquid reaction mixture which now contains a much lower syn gas concentration than was present in the reaction mixture leaving the hydroformylation reaction zone (the so-called hydroformylation reaction mixture) to the distillation zone e.g. vaporizer/separator, wherein the desired aldehyde product is distilled. In a preferred embodiment of the invention, at least a part of the hydroformylation reaction mixture or the liquid reaction mixture obtained by removing a substantial portion of unreacted carbon monoxide and hydrogen gases is exposed to a gaseous mixture comprising hydrogen or comprising hydrogen and carbon monoxide at an activating pressure greater than the partial pressure during the hydroformylation reaction. Without wishing to be bound to any theory it is believed to be advantageous to expose at least a part of the hydroformylation reaction mixture or at least a part of the reaction mixture obtained by removing from the hydroformylation reaction mixture a substantial portion of unreacted carbon monoxide and hydrogen to the gaseous mixture prior to distillation of such reaction mixture because the released alkadiene or hydroformylation product thereof can be separated in the distillation zone wherein the desired aldehyde is distilled and can be removed from the hydroformylation process together with the desired aldehyde product.

In an even more preferred embodiment of the invention, at least a part of the hydroformylation reaction mixture is exposed to a gaseous mixture comprising hydrogen or comprising carbon monoxide and hydrogen at an activating pressure which is greater than the partial pressure during the reaction.

In yet another preferred embodiment of the present invention the activating pressure of either hydrogen or hydrogen and carbon monoxide is between 3 and 20 MPa. More preferably it is between 3 and 10 MPa.

In another embodiment of the present invention, the activating pressure is maintained over a part of the reaction mixture in a vessel different from that containing the reaction mixture. Other objects and advantages of this invention will become readily apparent from the following written description and appended claims.

A rhodium bisphospite complex catalyzed hydroformylation reaction typically involves the exposure of an olefinically unsaturated compound to molecular hydrogen and carbon monoxide in the presence of a rhodium bisphospite complex catalyst, to obtain one or more product aldehydes. The olefinically unsaturated compounds employed in the hydroformylation process often contain impurities. Typical impurities include water, oxygen, and other olefinically unsaturated compounds. Among the most harmful impurities present within the olefinically unsaturated reactant are multi-unsaturated conjugated organic compounds. Included in this class of contaminants are compounds containing at least two alkene functionalities, such as alkadienes and alkatrienes. Especially the conjugated alkadienes and alkatrienes are harmful under normal hydroformylation conditions. Examples thereof are 1,3-butadiene, 1-vinyl cyclohexene, 1,3,7-octatriene. Such impurities are believed to react or complex with the rhodium organobisphosphite catalysts, or its precursors, in a competitive fashion. The rhodium-olefin complexes which result from these competitive impurity reactions are less reactive in catalyzing the desired hydroformylation reaction. As a result, the presence of these impurities often slows or halts the hydroformylation process. Thus the inventors of the present invention sought a means by which a rhodium complex catalyst may maintain its activity towards catalysis of the desired hydroformylation reaction.

As stated above, the subject invention resides in the discovery that alkadiene deactivation of such rhodium-organobisphosphite complex catalysts during the hydroformylation process, can be minimized or prevented by treating at least a portion of the reaction mixture with an activating pressure of hydrogen or of a mixture comprising carbon monoxide and hydrogen. The increase in the activating pressure may be performed intermittently or continuously, but is more preferably conducted in one or more discrete periods during the hydroformylation. If it is chosen to increase the partial pressure of carbon monoxide simultaneously with the partial pressure of hydrogen in order to achieve the activating pressure, then it is preferable to maintain this increase in carbon monoxide pressure for the same duration as the activating pressure of hydrogen is maintained.

In the present invention, the activating pressure may be maintained within the reaction vessel or within a separate vessel. If a separate vessel is employed, portions of the reaction mixture to be activated may be withdrawn and transferred to said separate vessel at any time during the hydroformylation process by any conventional manipulation, and then returned to the hydroformylation process following activation and preferably returned to the reaction zone of the hydroformylation process. Alternately, a continuous stream of reaction mixture may be withdrawn from the hydroformylation process and exposed to the activating pressure within a separate vessel, before being returned to the remainder of the reaction mixture. The term "reaction mixture" as used herein is understood to include the following substances present within the hydroformylation process: rhodium-organobisphosphite complex catalyst, solvent, and optionally unconverted olefinically unsaturated compound, any product aldehyde, carbon monoxide and hydrogen. The term "hydroformylation reaction mixture" as used herein is understood to include the following substances present within the hydroformylation process: rhodium-organobisphosphite complex catalyst, solvent, any unconverted olefinically unsaturated compound, any product aldehyde, and, optionally, carbon monoxide and hydrogen. With the term "hydroformylation reaction mixture" is meant the mixture which is obtained by reacting an olefinically unsaturated compound, carbon monoxide and hydrogen in the presence of a rhodium organobisphosphite complex catalyst.

Without wishing to be bound to any exact theory or mechanistic discourse, decreased catalytic activity of the rhodium-organobisphosphite complex in the presence of alkadienes most likely occurs as the result of the formation of coordinatively saturated rhodium-alkadiene complexes (second state catalyst complex). These complexes lack a means to coordinate another ligand, such as the olefinically unsaturated substrate, under typical hydroformylation conditions. However, under an activating pressure of carbon monoxide and hydrogen gas, these complexes may enter into a process by which the catalyst poisoning alkadiene ligand may itself be hydroformylated. As a result of this invention, the poisoning alkadiene is converted into for instance an aldehyde, thereby releasing active rhodium. The rhodium metal is than free to reenter the catalytic cycle as a reactive rhodium hydride or hydrido-carbonyl complex (first state catalyst complex). The second state catalyst complex is less effective in catalyzing the hydroformylation reaction than is the first state catalyst complex. Treating a mixture comprising at least a portion of the second state catalyst complex at a partial pressure of hydrogen or at a partial pressure of carbon monoxide and hydrogen which is greater than the sum of the partial pressures of hydrogen and carbon monoxide during the reaction allows for the catalyst complex to become in the first state.

The recuperation of the catalytic activity of the rhodium-organobisphosphite complex catalyst obtained according to this invention may be determined and confirmed by any suitable conventional procedure for ascertaining an increase in the productivity of the process. Preferably the process of this invention may be easily evaluated by carrying out comparative hydroformylation reactions and continuously monitoring their rates of hydroformylation. The difference in hydroformylation rate (or difference in catalyst activity) may then be observed in any convenient laboratory time frame. For instance, reaction rate may be expressed in terms of gram-moles of aldehyde product produced per liter of catalyst solution per hour of reaction, which rate, if desired, may be adjusted for varying olefin partial pressures by dividing said rate by the olefin partial pressure.

In a preferred embodiment of the present invention the rhodium-bisphosphite complex catalyst comprises a bisphosphite ligand of a formula selected from the group consisting of:

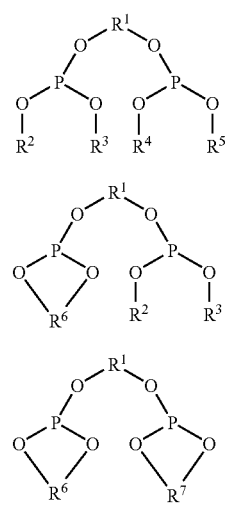

wherein each $R^1$ represents a divalent radical selected from a group consisting of alkylene, alkylene-$(Q)_n$-alkylene, arylene and arylene-$(Q)_n$-arylene, and wherein each alkylene radical individually contains from 2 to 18 carbon atoms and is the same or different, and wherein each arylene radical individually contains from 6 to 18 carbon atoms and is the same or different; wherein each Q individually represents a divalent bridging group of —O— or —CR'R"— wherein each R' and R" radical individually represents hydrogen or a methyl radical; and wherein each n individually has a value of 0 or 1, wherein $R^2$, $R^3$, $R^4$, and $R^5$ might be the same or different and each is individually represented by the structure of (VI) or (VII),

wherein $R^6$ and $R^7$ might be the same or different and each is individually represented by the structure of (VIII) or (IX),

wherein, $X^5$ and $X^6$ might be the same or different and each individually represents a hydrogen or an organic radical, wherein $Y^3$, $Y^4$ and $Y^5$ are the same or different and each represents a hydrogen or alkyl radical, wherein $Z^5$, $Z^6$, $Z^7$, $Z^8$, $Z^9$, $Z^{10}$ and $Z^{11}$ might be the same or different and each represent a hydrogen or an organic radical placed at any remaining position of the aryl rings.

In a more preferred embodiment of the present invention, $R^1$ is represented by the structure of (IV), (V),

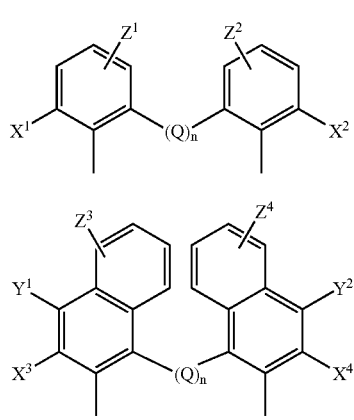

(VIII), (IX), wherein $(Q)_n$ is the same as above, wherein $X^1$, $X^2$, $X^3$, $X^4$, $X^5$ and $X^6$ might be the same or different and each individually represents a hydrogen or an organic radical, wherein $Y^1$, $Y^2$, $Y^4$ and $Y^5$ are the same or different and each represents a hydrogen or alkyl radical, wherein $Z^1$, $Z^2$, $Z^3$, $Z^4$, $Z^8$, $Z^9$, $Z^{10}$ and $Z^{11}$ might be the same or different and each represent a hydrogen or an organic radical placed at any remaining position of the aryl rings.

In an even more preferred embodiment of the present invention $R^1$ is represented by the structure of (IV), (V), (VIII), (IX), wherein $(Q)_n$ is the same as above, wherein $X^1$ is the same as $X^2$ and $Z^1$ is the same as $Z^2$ in Formula (IV), $X^3$ is the same as $X^4$, $Z^3$ is the same as $Z^4$, and $Y^1$ and $Y^2$ are hydrogen radicals in Formula (V), $Z^8$ is the same as $Z^9$ in Formula (VIII), $Z^{10}$ is the same as $Z^{11}$ and $Y^4$ and $Y^5$ are hydrogen radicals in Formula (IX).

Still more preferably said hydroformylation process is performed wherein said ligand used is chosen from the group consisting of [3,3'-bis(t-butyl)-5,5'-dimethoxy-1,1'-biphenyl-2,2'-diyl]-bis(oxy)]-bis(dibenzo[d,f] [1,3,2])dioxaphosphepin, 3,3'-bis(carboxyisopropyl)-1,1'-binaphthyl-2,2-diyl-bis[bis(1-naphthyl)]phosphite and 3,3'-bis(carboxymethyl)-1,1'-binaphthyl-2,2'-diyl-bis[bis(2,5-di-t-butyl)]phosphite.

Illustrative rhodium-bisphosphite complex catalysts employable in such hydroformylation reactions encompassed by this invention may include those disclosed in the above mentioned patents wherein the bisphosphite ligand is a ligand selected from the class consisting of Formulas (I), (II) and (III) above. In general, such catalysts may be preformed, or formed in situ, as described e.g., in said U.S. Pat. Nos. 4,668,651 and 4,769,498, and consist essentially of rhodium in complex combination with the organobisphosphite ligand. It is believed that carbon monoxide is also present and complexed with the rhodium in the active species. The active catalyst species may also contain hydrogen directly bonded to the rhodium.

As noted above illustrative organobisphosphite ligands that may be employed as the bisphosphite ligand complexed to the rhodium catalyst and/or any free bisphosphite ligand (i.e. ligand that is not complexed with the rhodium metal in the active complex catalyst) in such hydroformylation reactions encompassed by this invention include those of Formulas (I), (II), and (III) above.

Illustrative divalent radicals represented by $R^1$ in the above bisphosphite formulas (I), (II) and (III) include substituted and unsubstituted radicals selected from the group consisting of alkylene, alkylene-$(Q)_n$-alkylene, phenylene, naphthylene, phenylene-$(Q)_n$-phenylene and naphthylene-$(Q)_n$-naphthylene radicals, and where Q, and n are the same as defined above. More specific illustrative divalent radicals represented by $R^1$ are shown by the structure of (IV) or (V) wherein $(Q)_n$ is the same as above. These include, 1,1'-biphenyl-2,2'-diyl, 3,3'-dialkyl-1,1'-biphenyl-2,2'-diyl, 3,3'-dicarboxy ester-1,1'-biphenyl-2,2'-diyl, 1,1'binaphthyl-2,2'-diyl, 3,3'-dicarboxy ester-1,1'-binaphthyl-2,2'-diyl, 3,3'-dialkyl-1,1'-binaphthyl-2,2'-diyl, 2,2'-binaphthyl-1,1'-diyl, phenylene-$CH_2$-phenylene, phenylene-O-phenylene, phenylene-$CH(CH_3)$-phenylene radicals, and the like.

Illustrative radicals represented by $Z^1$, $Z^2$, $Z^3$, $Z^4$, $Z^5$, $Z^6$, $Z^7$, $Z^8$, $Z^9$, $Z^{10}$, and $Z^{11}$ in above Formulas (IV) to (IX), in addition to hydrogen, include any of those organic substituents containing from 1 to 18 carbon atoms, disclosed in U.S. Pat. No. 4,668,651, or any other radical that does not unduly adversely effect the process of this invention. Illustrative radicals and substituents encompass alkyl radicals, including primary, secondary and tertiary alkyl radicals such as methyl, ethyl n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; condensated aryl radicals such as phenylene, naphthylene, and the like, alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy —$OCH_2CH_2OCH_3$, —$O(CH_2CH_2)_2OCH_3$, —$O(CH_2CH_2)_3OCH_3$, and the like; aryloxy radicals such as phenoxy and the like; as well as silyl radicals such as —$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; acyl radicals such as —$C(O)CH_3$, —$C(O)C_2H_5$, —$C(O)C_6H_5$, and the like; carbonyloxy radicals such as —$C(O)OCH_3$, —$C(O)OCH(CH_3)_2$—$C(O)CH(CH_3)C_8H_{17}$, and the like; oxycarbonyl radicals such as —(CO)$C_6H_5$, and the like; amido radicals such as —$CONH_2$, —$CON(CH_3)_2$, —$NHC(O)CH_3$, and the like; sulfonyl radicals such as —$S(O)_2C_2H_5$ and the like; sulfinyl radicals such as —$S(O)CH_3$ and the like; thionyl radicals such as —$SCH_3$, —$SC_2H_5$, —$SC_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)CH_3(C_6H_5)$, —$P(O)(H)(C_6H_5)$, and the like.

Illustrative radicals represented by $X^1$, $X^2$, $X^3$, $X^4$, $X^5$ and $X^6$ in above Formulas (IV) to (IX) include those illustrated and discussed above as representing $Z^1$ to $Z^{11}$, except condensated aryl radicals.

Illustrative radicals represented by $Y^1$, $Y^2$, $Y^3$, $Y^4$ and $Y^5$ in above Formulas (IV) to (IX) include those illustrated and discussed above as representing $Z^1$ to $Z^{11}$, except condensated aryl radicals.

More preferably, $X^1$ is the same as $X^2$ and $Z^1$ is the same as $Z^2$ in Formula (IV), $X^3$ is the same as $X^4$, $Z^3$ is the same as $Z^4$, and $Y^1$, $Y^2$ are hydrogen radicals in Formula (V), $Z^6$ is a hydrogen radical in Formula (VII), $Z^8$ is the same as $Z^9$ in Formula (VIII), $Z^{10}$ is the same as $Z^{11}$ and $Y^4$ and $Y^5$ are hydrogen radicals in Formula (IX).

Specific illustrative examples of the bisphosphite ligands employable in this invention include such preferred ligands as:

3,3'-bis(carboxyisopropyl)-1,1'-binaphthyl-2,2'-diyl-bis[bis(1-naphthyl)]phosphite having the formula:

(XII)

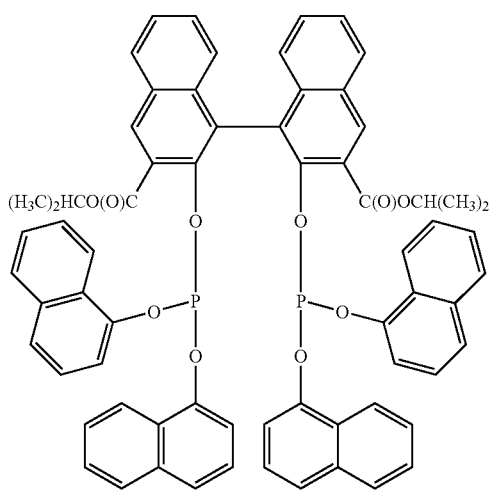

[3,3'-bis(t-butyl)-5,5'-dimethoxy-1,1'-biphenyl-2,2'diyl]-bis(oxy)]-bis(dibenzo[d,f] [1,3,2)dioxaphosphepin having the formula:

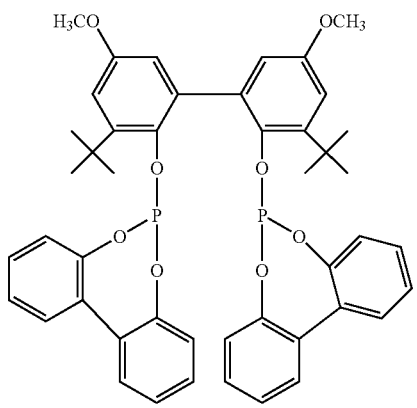

3,3'-bis(carboxyisopropyl)-1,1'-binaphthyl-2-yl-bis[(1-naphthyl))]phosphite-2'-yl-oxy-dibenzo[d,f] [1,3,2]dioxaphosphepin having the formula:

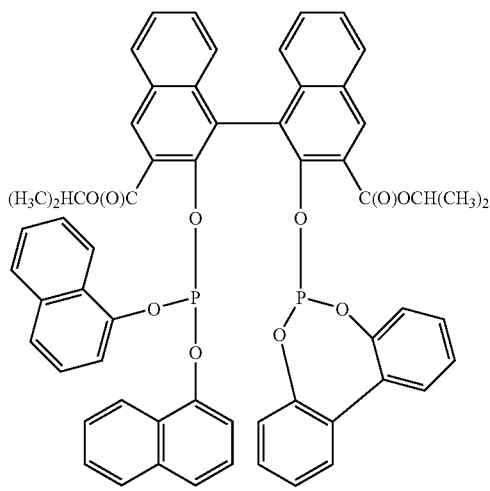

5,5'-bis(t-butyl)-3,3'-dimethoxy-1,1'-biphenyl-2,2'-diyl-bis[bis(1-naphthyl)]phosphite having the formula:

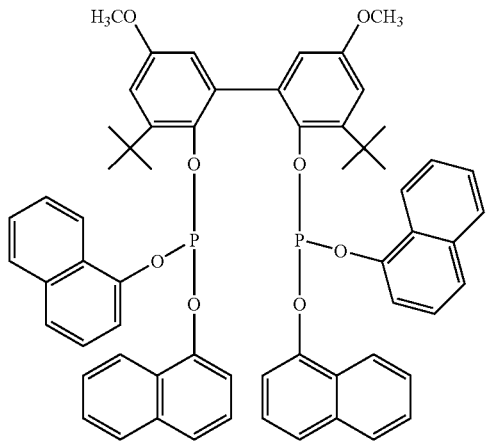

3,3'-bis(carboxymethyl)-1,1'-binaphthyl-2,2'-diyl-bis[bis(2-t-butylphenyl)]phosphite having the formula:

[3,3'-bis(t-butyl)-5,5'-dimethoxy-1,1'-biphenyl-2,2'-diyl]-bis(oxy)]-bis([1,1'-dinaphto[d,f] [1,3,2])dioxaphosphepin having the formula:

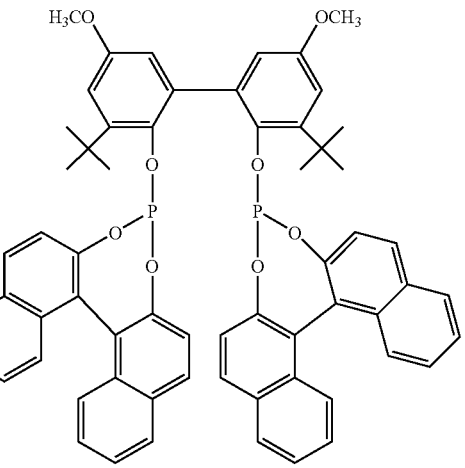

and the like.

Such types of bisphosphite ligands employable in this invention and/or methods for their preparation are well known as seen disclosed for example in U.S. Pat. Nos. 4,668,651; 5,288,918; 5,710,306, the entire disclosure of which is incorporated herein by reference thereto.

In general, such hydroformylation reactions involve the production of aldehydes by reacting an olefinically unsaturated compound with carbon monoxide and hydrogen in the presence of a rhodium-organobisphosphite complex catalyst in a liquid medium that also contains a solvent for the catalyst. The process may be carried out in a continuous single pass mode or more preferably in a continuous liquid catalyst recycle manner. The recycle procedure generally involves withdrawing a portion of the liquid reaction mixture containing the catalyst and aldehyde product from the hydroformylation reaction zone, either continuously or intermittently, and distilling aldehyde product therefrom in one or more stages, in a separate distillation zone in order to recover aldehyde product and other volatile materials in vaporous form, the non-volatilized rhodium catalyst containing residue being recycled to the reaction zone. Likewise, the recovered non-volatilized rhodium catalyst containing residue can be recycled with or without further treatment to the hydroformylation zone in any conventional manner desired. Accordingly, the processing techniques of this invention may correspond to any known processing techniques such as heretofore employed in conventional liquid catalyst recycle hydroformylation reactions.

As noted above the hydroformylation reaction conditions that may be employed in the hydroformylation processes encompassed by this invention may include any suitable continuous hydroformylation conditions heretofore disclosed in the above-mentioned patents. Further, the hydroformylation process may be conducted at a reaction temperature from about 25° C. to about 150° C. In general hydroformylation reaction temperature of about 70° C. to about 120° C. are preferred for all types of olefinic starting materials, the more preferred reaction temperatures being from about 90° C. to about 100° C. and most preferably about 95° C.

The olefinic starting material reactants that may be employed in the hydroformylation reactions encompassed by this invention include olefinic compounds containing from 2 to 30 carbon atoms. Such olefinic compounds can be terminally or internally unsaturated and be of straight-chain, branched chain or cyclic structures, as well as be olefin mixtures, such as obtained from the oligomerization of propene, butene, isobutene, etc., (such as so called dimeric, trimeric or tetrameric propylene, and the like, as disclosed, e.g., in U.S. Pat. Nos. 4,518,809 and 4,528,403). Moreover, mixtures of two or more different olefinic compounds may be employed as the starting hydroformylation material if desired. Further such olefinic compounds and the corresponding aldehyde products derived therefrom may also contain one or more groups or substituents which do not unduly adversely affect the hydroformylation process or the process of this invention such as described, e.g., in U.S. Pat. Nos. 3,527,809; 4,668,651 and the like.

Illustrative olefinic unsaturated compounds are alpha-olefins, internal olefins, alkyl alkenoates such as methyl-2-pentenoate, methyl-3-pentenoate and methyl-4-pentenoate, alkenyl alkanoates, alkenyl alkyl ethers, alkenols, and the like, e.g., ethene, propene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexene, 2-heptene, cyclohexene, 2-ethyl-1-hexene, 2-octene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 3-pentenenitrile and 5-hexenamide.

Of course, it is understood that mixtures of different olefinic starting materials can be employed, if desired, by the hydroformylation process of the subject invention. More preferably the subject invention is especially useful for the production of aldehydes, by hydroformylating alpha olefins containing from 2 to 20 carbon atoms, including isobutylene, and internal olefins containing from 4 to 20 carbon atoms as well as starting material mixtures of such alpha olefins and internal olefins. Still more preferably the subject invention is especially useful for the production of aldehydes from methyl-3-pentenonate, in any isomeric form, or mixture of isomeric forms.

As noted above the hydroformylation reaction conditions that may be employed in the hydroformylation processes encompassed by this invention may include any suitable continuous hydroformylation conditions heretofore disclosed in the above-mentioned patents. For instance, the total gas pressure of hydrogen, carbon monoxide and olefinic unsaturated starting compound of the hydroformylation process may range from about 1 to about 10,000 psia. In general, however, it is preferred that the process be operated at a total gas pressure of hydrogen, carbon monoxide and olefinic unsaturated starting compound of less than about 1500 psia and more preferably less than about 500 psia. The minimum total pressure being limited predominately by the amount of reactants necessary to obtain a desired rate of reaction. More specifically the carbon monoxide partial pressure of the hydroformylation process of this invention is preferable from about 1 to about 120 psia, and more preferably from about 3 to about 90 psia, while the hydrogen partial pressure is preferably about 15 to about 160 psia and more preferably from about 30 to about 100 psia. In general $H_2$:CO molar ratio of gaseous hydrogen to carbon monoxide may range from about 1:10 to 100:1 or higher, the more preferred hydrogen to carbon monoxide molar ratio being from about 1:10 to about 10:1. The term syn-gas as used herein is understood to mean any gaseous mixture comprised of hydrogen and carbon monoxide.

As noted above, the continuous hydroformylation process of this invention involves the use of a rhodium-organobisphosphite ligand complex catalyst as described herein. Of course mixtures of such catalysts can also be employed if desired. The amount of rhodium-phosphite complex catalyst present in the reaction mixture of a given hydroformylation process encompassed by this invention need only be that minimum amount necessary to provide the given rhodium concentration desired to be employed and which will furnish the basis for at least the catalytic amount of rhodium necessary to catalyze the particular hydroformylation process involved such as disclosed e.g. in the above-mentioned patents. In general, rhodium concentrations in the range of from about 10 ppm to about 1000 ppm, calculated as free rhodium, in the reaction mixture should be sufficient for most processes, while it is generally preferred to employ from about 10 to 500 ppm of rhodium and more preferably from 25 to 350 ppm to rhodium.

In addition to the rhodium-organobisphosphite catalyst the hydroformylation process encompassed by this invention may be carried out in the presence of free organobisphosphite ligand, i.e. ligand that is not complexed with the rhodium metal of the complex catalyst employed. Said free organobisphosphite ligand may correspond to any of the above defined organobisphosphite ligands discussed above as employable herein. When employed it is preferred that the free organobisphosphite ligand be the same as the organobisphosphite ligand of the rhodium-organobisphosphite complex catalyst employed. However, such ligands need not be the same in any given process. Moreover, while it may not be absolutely necessary for the hydroformylation process to be carried out in the presence of any such free organobisphosphite ligand, the presence of at least some amount of free organobisphosphite ligand in the reaction mixture is preferred. Thus the hydroformylation process of this invention may be carried out in the absence or presence of any amount of free organobisphosphite ligand, e.g. up to 100 moles, or higher per mole of rhodium metal in the reaction mixture. Preferably the hydroformylation process of this invention is carried out in the presence of from about 1 to about 50 moles of organobisphosphite ligand, and more preferably from about 1 to about 4 moles of organobisphosphite ligand, per mole of rhodium metal present in the reaction mixture; said amounts of organobisphosphite ligand being the sum of both the amount of organobisphosphite ligand that is bound (complexed) to the rhodium metal present and the amount of free (non-complexed) organobisphosphite ligand present. Of course, if desired, make-up or additional organobisphosphite ligand can be supplied to the reaction mixture of the hydroformylation process at any time and in any suitable manner, e.g. to maintain a predetermined level of free ligand in the reaction mixture.

The hydroformylation reactions encompassed by this invention may also be conducted in the presence of an organic solvent for the rhodium-organobisphosphite complex catalyst and any free organobisphosphite ligand that might be present. Any suitable solvent which does not unduly adversely interfere with the intended hydroformylation process can be employed. Illustrative suitable solvents for rhodium catalyzed hydroformylation processes include those disclosed e.g. in U.S. Pat. No. 4,668,651. Of course mixtures of one or more different solvents may be employed if desired. Most preferably the solvent will be one in which the olefinic starting material, and catalyst, are all substantially soluble. In general, it is preferred to employ aldehyde compounds corresponding to the aldehyde products desired to be produced and/or higher boiling aldehyde liquid condensation by-products as the primary solvent, such as the higher boiling aldehyde liquid condensation by-products that are produced in situ during the hydroformylation process. Indeed, while one may employ any suitable solvent at the start up of a continuous process, the primary solvent will normally eventually comprise both aldehyde products and higher boiling aldehyde liquid condensation by-products due to the nature of such continuous processes. Such aldehyde condensation by-products can also be preformed if desired and used accordingly. Of course, the amount of solvent employed is not critical to the subject invention and need only be that amount sufficient to provide the reaction mixture with the particular rhodium concentration desired for a given process. In general, the amount of solvent may range from 0 percent by weight up to about 95 percent by weight or more based on the total weight of the reaction mixture.

The distillation and separation of the desired aldehyde product from the rhodium-bisphosphite complex catalyst containing product solution may take place at any suitable temperature desired. In general it is recommended that such distillation take place at low temperatures, such as below 150° C., and more preferably at a temperature in the range of from about 50° C. to about 130° C., and most preferably between 70 and 115° C. It is also generally recommended that such aldehyde distillation takes place under reduced pressure, e.g. a total gas pressure that is substantially lower than the total gas pressure employed during hydroformylation when low boiling aldehydes (e.g. $C_4$ to $C_6$) are involved or under vacuum when high boiling aldehydes (e.g. $C_7$ or greater) are involved. In general distillation pressures ranging from vacuum pressures or below on up to total gas pressure of about 50 psig should be sufficient for most purposes.

Of course it is to be understood that while the optimization of the subject invention necessary to achieve the best results and efficiency desired are dependent upon one's experience in the utilization of the subject invention, only a certain measure of experimentation should be necessary to ascertain those conditions which are optimum for a given situation and such should be well within the knowledge of one skilled in the art and easily obtainable by following the more preferred aspects of this invention as explained herein and/or by simple routine experimentation.

Finally, the aldehyde products of the hydroformylation process of this invention have a wide range of utility that is well known and documented in the prior art e.g. they are especially useful as starting materials for the production of alcohols and acids, as well as for the production of monomeric and polymeric compounds such as ε-caprolactam, adipic acid, nylon-6 and nylon-6,6.

The following examples are illustrative of the present invention and are not be regarded as limitive. It is to be understood that all of the parts, percentages and proportions referred to herein and in the appended claims are by weight unless otherwise indicated.

EXAMPLE 1

In a continous process, methyl-3-pentenoate was hydroformylated using a rhodium/naftol-3 (ligand with structure XII) catalyst. The reaction temperature was 95° C. and the pressure was 0.5 MPa. The molar ratio of hydrogen to carbon monoxide was 1:1. A rhodium concentration of 150 ppmw was applied with a small molar excess of ligand (ligand/Rh=1.1). The ligand concentration was kept at a constant level by continuous feed of make-up ligand to the reactor. The average hold-up time in the stirred continuous tank reactor was approximately 4 hours. The liquid reactor effluent was flashed to atmospheric pressure to removed a large part of the dissolved gasses. After this flash, the liquid was passed to a vacuum evaporator where most of the unconverted substrates and the aldehyde products were removed as overheads. The overhead products were collected and analyzed by Gas chromatographic techniques. The bottom stream, containing the non volatile catalyst was continuously recycled to the reactor. During the run the conversion was determined to be 84% to methyl-5-formylvalerate. The STY (space time yield) was estimated at 0.65 mole M5FV/ltr.hr.

Comparative Experiment A

Performed as described in Example 1 using a methyl-3-pentenoate feed that was contaminated with trace amounts of 1,3-butadiene (250 ppm). The catalyst activity reduced to 0.05 mole M5FV/ltr.hr and hence the catalyst showed negligible activity.

EXAMPLE 2

Comparative Experiment A was continued by reducing the methyl-pentenoate feed to a stop, and to raise the pressure of the reactor to 7 MPa for 2 cycles, i.e. the time required for the whole catalyst inventory to spend the 4 hour hold-up time in the reactor, to pass the separation, section, and to recycle back to the reactor. Then the pressure was reduced to 0.5 MPa and the feed was re-started using the non-contaminated methyl-3-pentenoate, initially at such a rate sufficient to restore the initial catalyst concentration. The catalyst activity was recovered to the normal value of STY of 0.6 mole M5FV/ltr.hr.

The invention claimed is:

1. A continuous hydroformylation process for producing an aldehyde comprising 1) reacting an olefinically unsaturated compound, carbon monoxide and hydrogen in the presence of a rhodium-organobisphosphite complex catalyst at a partial pressure of carbon monoxide and hydrogen, and 2) exposing a mixture comprising at least a portion of the catalyst of 1) to a gaseous mixture comprising hydrogen at a pressure that is greater than the partial pressure of carbon monoxide and hydrogen during the reaction.

2. Process according to claim 1, wherein the gaseous mixture comprises hydrogen and carbon monoxide.

3. Process according to claim 1, wherein aldehyde product is separated from the catalyst by distilling the hydroformylation reaction mixture and wherein at least a part of the hydroformylation reaction mixture is exposed to the gaseous mixture prior to distillation.

4. The process according to claim 1, wherein the pressure used in step 2) is between 3 and 20 MPa.

5. The process according to claim 4, wherein the pressure used in step 2) is between 3 and 10 MPa.

6. The process according to claim 1, wherein step 2) is performed in a vessel which is separate from the reaction vessel.

7. A hydroformylation process comprising:
a) reacting an olefinically unsaturated compound, with carbon monoxide and hydrogen at a partial pressure of hydrogen and carbon monoxide in the presence of a rhodium-organobisphosphite complex catalyst to produce a hydroformylation reaction mixture,
b) separating aldehyde product from catalyst by heating the hydroformylation reaction mixture, resulting in an aldehyde product containing stream and a recyclable catalyst containing stream, wherein at least a portion of the hydroformylation reaction mixture and/or a portion of the recyclable catalyst containing stream is treated with a gaseous mixture comprising hydrogen at a partial pressure greater than the partial pressures in a).

8. The process according to claim 1, wherein the organobisphosphite ligand of said rhodium-organobisphosphite complex catalyst is a ligand selected from the class consisting of

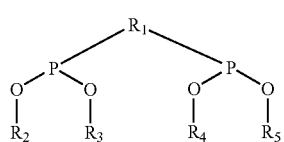

(I)

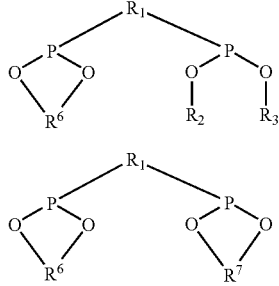

(II)

(III)

wherein each $R^1$ represents a divalent radical selected from a group consisting of alkylene, alkylene-$(Q)_n$-alkylene, arylene and arylene-$(Q)_n$-arylene, and wherein each alkylene radical individually contains from 2 to 18 carbon atoms and is the same or different, and wherein each arylene radical individually contains from 6 to 18 carbon atoms and is the same or different; wherein each Q individually represents a divalent bridging group of —O— or —CR'R"— wherein each R' and R" radical individually represents hydrogen or a methyl radical; and wherein each n individually has a value of 0 or 1, wherein $R^2$, $R^3$, $R^4$, and $R^5$ might be the same or different and each is individually represented by the structure of (VI) or (VII),

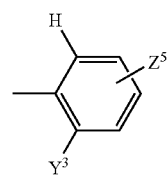

(VI)

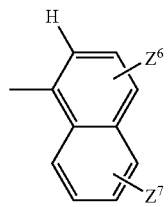

(VII)

wherein $R^6$ and $R^7$ might be the same or different and each is individually represented by the structure of (VIII) or (IX),

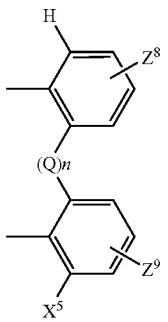

(VIII)

-continued

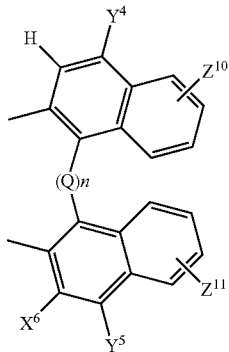
(IX)

wherein, $X^5$ and $X^6$ might be the same or different and each individually represents a hydrogen or an organic radical, wherein $Y^3$, $Y^4$ and $Y^5$ are the same or different and each represents a hydrogen or alkyl radical, wherein $Z^5$, $Z^6$, $Z^7$, $Z^8$, $Z^9$, $Z^{10}$ and $Z^{11}$ might be the same or different and each represent a hydrogen or an organic radical placed at any remaining position of the aryl rings.

9. The process of claim 8, wherein $R^1$ is represented by the structure of (IV), (V), (VIII) or (IX),

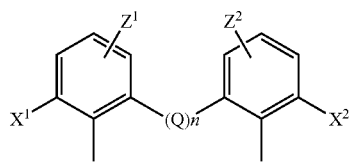
(IV)

-continued

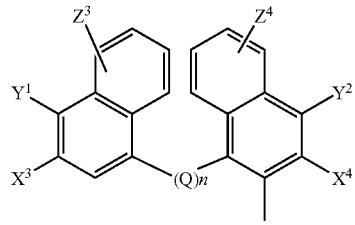
(V)

wherein $X^1$, $X^2$, $X^3$, $X^4$, $X^5$ and $X^6$ might be the same or different and each individually represents a hydrogen or an organic radical, wherein $Y^1$, $Y^2$, $Y^4$ and $Y^5$ are the same or different and each represents a hydrogen or an alkyl radical, wherein $Z^1$, $Z^2$, $Z^3$, $Z^4$, $Z^8$, $Z^9$, $Z^{10}$ and $Z^{11}$ might be the same or different and each represent a hydrogen or an organic radical placed at any remaining position of the aryl rings of structures, wherein $X^1$ is the same as $X^2$ and $Z^1$ is the same as $Z^2$ in Formula (IV), $X^3$ is the same as $X^4$, $Z^3$ is the same as $Z^4$, and $Y^1$ and $Y^2$ are hydrogen radicals in Formula (V), $Z^8$ is the same as $Z^9$ in Formula (VIII), $Z^{10}$ is the same as $Z^{11}$ and $Y^4$ and $Y^5$ are hydrogen radicals in Formula (IX).

10. The process according to claim 8, wherein the ligand used is [3,3'-bis(t-butyl)-5,5'-dimethoxy-1,1'-biphenyl-2,2'-diyl]-bis(oxy)]-bis(dibenzo[d,f][1,3,2])dioxaphosphepin, 3,3'-bis(carboxyisopropyl)-1,1'-binaphthyl-2,2-diyl-bis[bis(1-naphthyl)]phosphite and 3,3'-bis(carboxymethyl)-1,1'-binaphthyl-2,2'-diyl-bis[bis(2,5-di-t-butyl)]phosphite.

* * * * *